United States Patent
Staehle et al.

(10) Patent No.: US 6,464,960 B1
(45) Date of Patent: Oct. 15, 2002

(54) WATER-CONTAINING AEROSOL HAIR SPRAY WITH A REDUCED CONTENT OF VOLATILE ORGANIC COMPOUNDS

(75) Inventors: Liane Staehle, Ober-Ramstadt; Ulrich Herfurt, Mainz, both of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/615,536

(22) Filed: Jul. 13, 2000

Related U.S. Application Data
(60) Provisional application No. 60/146,659, filed on Aug. 2, 1999.

(30) Foreign Application Priority Data

Jul. 23, 1999 (DE) .......................................... 199 34 701

(51) Int. Cl.⁷ ............................. A61K 7/11; A61K 7/06; A61K 9/12; A61K 9/14; B05B 9/04
(52) U.S. Cl. .................. 424/47; 424/70.11; 424/DIG. 1; 424/DIG. 2; 424/484; 514/724; 514/937; 514/957; 514/675; 514/715; 239/337; 239/372; 239/573; 239/373
(58) Field of Search ..................... 424/47, 484, DIG. 1, 424/DIG. 2, 70.11; 514/724, 937, 957, 675, 715; 239/337, 372, 573, 373

(56) References Cited

U.S. PATENT DOCUMENTS

| | | | |
|---|---|---|---|
| 3,790,089 A | | 2/1974 | Frangos |
| 4,230,243 A | | 10/1980 | Spitzer et al. |
| 4,243,548 A | | 1/1981 | Heeb et al. |
| 5,599,524 A | * | 2/1997 | Morawsky et al. ............ 424/47 |
| 5,853,700 A | * | 12/1998 | Gormley et al. .............. 424/47 |

OTHER PUBLICATIONS

Aerosol and Spray Report, vol. 35, No. 5/96, pp. 256–259.
Aerosol and Spray Report, vol. 37, No. 6/98, p. 14–23.

* cited by examiner

*Primary Examiner*—Frederick Krass
*Assistant Examiner*—Clinton Ostrup
(74) *Attorney, Agent, or Firm*—Michael J. Striker

(57) ABSTRACT

The aerosol hair spray composition contains a hair-setting polymer in a solvent/propellant system containing a $C_1$ to $C_4$ alcohol, water, a cosolvent selected from among acetone and methyl acetate or a mixture thereof, and aerosol propellants, particularly a combination of dimethyl ether and a fluorocarbon. The composition according to the invention makes it possible to produce low-cost, water-containing aerosol hair sprays with a reduced VOC content and at the same time to optimize their use properties.

8 Claims, No Drawings

WATER-CONTAINING AEROSOL HAIR SPRAY WITH A REDUCED CONTENT OF VOLATILE ORGANIC COMPOUNDS

CROSS-REFERENCE

This application claims the benefit of U.S. Provisional Application Ser. No. 60/146,659 filing date Aug. 2, 1999.

BACKGROUND OF THE INVENTION

1. Field of the Invention

The present invention relates to is a water-containing aerosol hair spray containing hair-setting polymers and a specially selected mixture of solvents and propellants, wherein the substances classified as VOC (volatile organic compounds) are preferably contained in a maximum amount of 55%.

2. Prior Art

Aerosol hair sprays were and are commonly used in the form of polymer solutions or polymer dispersions in an alcoholic medium. These conventional hair sprays containing high amounts of VOC are characterized by outstanding product and use properties. From the standpoint of environmental protection and in view of anticipated legal regulations, there is a need for reducing as much as possible the amount of VOC in hair sprays including, among other compounds, also the alcoholic solvents, such as ethanol and isopropanol and the common propellants such as, propane, butane or dimethyl ether which until now have commonly been used in hair sprays.

Products with a maximum VOC content of 80% are already known. As a rule, however, the use properties of these 80% VOC formulations are clearly worse than those of conventional hair sprays, and the performance is only just acceptable or deficient (Aerosol and Spray Report, vol. 35, No. 5/96, page 254 ff.). They give less hold and cause more complaints and a general business downturn. For the 55% VOC formulations, more problems are expected, and it is anticipated that either a further deterioration in use properties or a marked increase in cost will have to be accepted. Known approaches to 55% VOC formulations are based either on an increased water content in combination with dimethyl ether or propane/butane or a dimethyl ether/butane mixture as propellants or on water-free formulations in combination with propellants classified as non-VOC, namely 1,1-difluoroethane or 1,1,1,2-tetrafluoroethane. The currently known 55% VOC formulations, however, do not have the outstanding use properties of conventional water-free hair sprays with a high VOC content. An increased water content causes multiple problems, for example less hair hold, higher curl droop effect, higher degree of wetness, higher tack of the polymer film during the drying phase, larger drop size of the spray, inferior spray pattern, foaming during spraying, higher viscosity with an attendant inferior sprayability, longer drying time, lack of resistance to hydrolysis and corrosion, inferior compatibility with solvents, cosolvents, propellants and/or polymers, which manifests itself in inferior storage stability, inferior cold resistance or in the formation of turbidity, precipitates or several liquid phases Thus far, end users and hair dressers have always rated the main criteria of aqueous or aqueous-alcoholic hair sprays, namely hair setting, hair crosslinking, feel (stiffness, tack, smoothness) and drying time as unacceptably inferior. The exclusive use of fluorocarbons as non-VOC propellants in water-free formulations has the drawback that such formulations are highly cost-intensive because of the high price of fluorocarbons. Acetone is currently not used in hair spray formulations as replacement for the otherwise commonly employed lower alcohol solvents (Aerosol and Spray Report, vol. 37, No. 6/98, page 18), because acetone has a number of serious drawbacks: it has an unacceptable odor that cannot be masked with perfume; it evaporates too quickly so that the sprayed-on solution does not adequately flow on the hair resulting in inferior crosslinking and inferior setting; polymers that are readily soluble in water or water/alcohol are not soluble or are only insufficiently soluble in acetone; polymers soluble in water/acetone are often sparingly soluble in water and, hence, during the rapid evaporation of acetone precipitate onto the hair too rapidly before a film can form, which results in inferior hair setting.

SUMMARY OF THE INVENTION

Hence it is an object of the invention was to optimize further the properties of water-containing aerosol hair sprays with a reduced VOC content and to approximate as much as possible the properties of conventional water-free hair sprays with a high VOC content without excessively increasing formulation costs.

It has now been found that this objective can be reached by use of a water-containing aerosol hair spray comprising hair-setting polymers and a special combination of certain selected solvents and propellants, preferably in certain selected amounts.

Hence, the object of the invention is an aerosol attained by hair spray consisting of a hair spray composition, a pressurized container for containing the hair spray composition and a spraying or valve device for dispensing the hair spray composition from the container, the composition according to the invention, the composition according to the invention containing (A) at least one hair-setting polymer,
(B) 10 to 40 wt % of at least one alcohol with 1 to 4 carbon atoms,
(C) 10 to 30 wt % of water,
(D) 1 to 30 wt % of at least one cosolvent selected from the group consisting of acetone, methyl acetate or a mixture thereof, and
(E) 20 to 75 wt % of at least one propellant, said propellant preferably being a combination of 15 to 45 wt % (based on the total composition) of dimethyl ether and 5 to 30 wt % (based on the total composition) of at least one propellant classified as non-VOC, selected from among fluorocarbons.

The present invention is eminently suited to the preparation of formulations with a reduced content of-organic volatile compounds (VOC), for example of VOC 80% or VOC 55% formulations. The composition according to the invention therefore contains a maximum of 80 wt % and particularly a maximum of 55 wt % of constituents classified as VOC. The California Air Resources Board (CARB) defines VOC as substances with a vapor pressure of >0.1 mm Hg at 20°C. or as substances with 12 or less carbon atoms. On the basis of this definition, a number of substances, for example carbon dioxide, methylene chloride, acetone, methyl acetate, fluorochloro-carbons and fluorocarbons are excluded because of their low or zero photochemical ozone creation potential (POCP).

The hair-setting polymer is preferably contained in the composition according to the invention in an amount from 3 to 20 wt % and particularly from 5 to 10 wt %. Suitable polymers are nonionic, anionic or amphoteric polymers soluble in the solvent/propellant mixture of the invention, and particularly copolymers derived from at least one hydrophilic and at least one hydrophobic monomer.

Suitable anionic polymers are the synthetic homopolymers or copolymers containing monomer units with neutralizable acid groups, optionally copolymerized with comonomers devoid of acid groups. Suitable acid groups are sulfonic, phosphoric and carboxylic acid groups among which carboxylic groups are preferred. Suitable acid groups-containing monomers are, for example, acrylic, methacrylic, crotonic and maleic acid or maleic anhydride, aldehydocarboxylic acids or ketocarboxylic acids.

Comonomers not substituted with acid groups are, for example, acrylamide, methacrylamide, alkyl- and dialkylacrylamide, alkyl- and dialkylmethacrylamide, alkyl acrylate, alkyl methacrylate, vinylcaprolactone, vinylpyrrolidone, vinyl esters, vinyl alcohol, propylene glycol or ethylene glycol, amino-substituted vinyl monomers, for example dialkylaminoalkyl acrylate, dialkylaminoalkyl methacrylate, monoalkylaminoalkyl acrylate and monoalkylaminoalkyl methacrylate, the alkyl groups of these monomers preferably being $C_1$ to $C_7$ alkyl groups and particularly $C_1$ to $C_3$ alkyl groups.

Suitable anionic polymers are, in particular, non-crosslinked homopolymers of acrylic acid or methacrylic acid or homopolymers of said acids crosslinked with a polyfunctional agent, furthermore the copolymers of acrylic acid or methacrylic acid and monomers selected from the group consisting of acrylate or methacrylate esters, acrylamides, methacrylamides and vinylpyrrolidone, homopolymers of crotonic acid and copolymers of crotonic acid and monomers selected from among the vinyl esters, acrylate or methacrylate esters, acrylamides and methacrylamides. A suitable natural anionic polymer is, for example, partly or totally neutralized shellack.

Preferred acid groups-containing polymers are the crosslinked or noncrosslinked vinyl acetate/crotonic acid copolymers, marketed, for example, in the form of a 60% solution in isopropanol/water by Hoechst/Germany under the tradename ARISTOFLEX® or by BASF under the tradename LUVISET® CA-66. Other suitable anionic polymers are, for example, the terpolymers of vinyl acetate, crotonic acid and polyethylene oxide and the terpolymers of acrylic acid, alkyl acrylate and N-alkylacrylamide, particularly acrylic
-acid/ethyl acrylate/N-t-butylacrylamide terpolymers such as those marketed by BASF/Germany under the names ULTRAHOLD® 8 and ULTRAHOLD® STRONG, or the terpolymers of vinyl acetate, crotonate and vinyl alkanoate, particularly vinyl acetate/crotonate/vinyl neodecanoate copolymers, for example those marketed by National Starch under the tradename RESYN 28-2930, or vinyl acetate/crotonate/vinyl propionate copolymers.

Another class of suitable anionic polymers are anionic polyurethanes. Preferred polyurethanes are characterized in that they contain (a) terminal acid groups introduced, for example, with the aid of aminosulfonic groups or aminocarboxylic groups, (b) optionally other free carboxylic acid groups introduced by use of carboxylic acid diols, for example dimethylolpropanoic acid, as comonomers, and (c) polyurethane sequences derived from polyester diols and diisocyanates, for example alkylene diisocyanates or isophorone diisocyanate. Suitable is, for example, Luviseto® PUR supplied by BASF/Germany.

The anionic polymers present in the composition according to the invention are partly or totally neutralized with a neutralizing agent compatible with cosmetics. Suitable neutralizing agents are organic or inorganic bases. Examples of such bases are, in particular, amino alcohols, for example aminomethylpropanol (AMP), triethanolamine or monoethanolamine, as well as ammonia, NaOH etc.

Suitable nonionic, hair-setting polymers are, for example, the homopolymers and copolymers derived from at least one nonionic monomer. Nonionic monomers are, for example, acrylamide, methacrylamide, alkyl- and dialkylacrylamide, alkyl- and dialkylmethacrylamide, alkyl acrylate, alkyl methacrylate, vinylcaprolactone, vinylpyrrolidone, vinyl esters, vinyl alcohol, propylene glycol or ethylene glycol, wherein the alkyl groups of these monomers are preferably $C_1$ to $C_7$ alkyl groups and particularly $C_1$ to $C_3$ alkyl groups. Suitable synthetic, nonionic, hair-setting polymers are, for example, the homopolymers of vinylpyrrolidone and the homopolymers of N-vinylformamide. Other suitable synthetic film-forming, nonionic, hair-setting polymers are, for example, the copolymers of vinyl pyrrolidone and vinyl acetate, the terpolymers of vinyl pyrrolidone, vinyl acetate and vinyl propionate, and the polyacrylamides, polyvinyl alcohols or polyethylene glycols with a molecular weight of 800 to 20,000 g/mol.

Suitable amphoteric polymers are those containing both cationic groups or groups that are cationizable by protonation, and anionic groups or groups that are anionizable by deprotonation. Cationic groups are, for example, quaternary amino groups, and cationizable groups are, for example, primary, secondary or tertiary amino groups. Anionic groups are, for example, carboxylate, sulfate, sulfonate, phosphate or phosphonate groups. Anionizable groups are, for example, the protonized forms of said anionic groups.

Suitable amphoteric polymers are, for example, the copolymers of octylacrylamide, tert. butylaminoethyl methacrylate and two or more monomers consisting of acrylic acid, methacrylic acid or their esters, wherein at least one of the acrylate monomers bears a nonesterified acid group.

The following hair-setting polymers were found to be most effective in the hair spray of the invention: polyvinylpyrrolidone/vinyl acetate copolymer, the copolymers of octylacrylamide, tert.butylaminoethyl methacrylate and two or more monomers consisting of acrylic acid, methacrylic acid or the esters thereof wherein at least one of the acrylate monomers bears a nonesterified acid group (Amphomer®), vinylpyrrolidone/vinylcaprolactam/dialkylaminoalkylmethacrylamide copolymers and acrylate co-polymers wherein a first, hydrophilic type of monomer is selected from among acrylic acid and methacrylic acid or hydroxy-substituted esters of acrylic acid or methacrylic acid, and a second, hydrophobic type of monomer is selected from among esters of acrylic acid or methacrylic acid (INCI[1]: acrylates copolymer, acrylates/hydroxy ester acrylate copolymer), for example a terpolymer of butyl acrylate, methyl methacrylate and methacrylic acid or a terpolymer of butyl acrylate, methyl methacrylate and 2-hydroxyethyl methacrylate.

Particularly preferred polymers are the polymers with the INCI designation acrylates copolymers and an acidity of 1.4 to 1.6 meq/g, for example Balance® CR or Balance® Extra, supplied by National Starch, which are marketed in the form of 45% aqueous emulsions, or the polymers with the INCI designation acrylates/hydroxy ester acrylate copolymer, for example Acudyne® 258, supplied by Rohm & Haas. Other particularly preferred hair-setting polymers are the terpolymers of vinylpyrrolidone, vinylcaprolactam and dimethylaminopropylmethacrylamide (DMAPMA) containing 1–25 wt % and preferably 5 to 15 wt % of vinylpyrrolidone units, 60 to 95 wt % and preferably 80 to 90 wt % of vinylcaprolactam units and 1 to 10 wt % and preferably 2.5 to 7.5 wt % of DMAPMA units. The synthesis of these terpolymers is described in WO 96/19971. A suitable terpolymer is, for example, Aquaflex SF-40®, supplied by ISP, which is marketed with a 40% solids content in ethanol.

According to the invention, the solvent mixture used consists of water, lower alcohols and certain cosolvents the properties of which are further modified by the partial solubility of the dimethyl ether propellant (up to 35% in water) and the fluorocarbons (1,1-difluoroethane up to 1.7% in water). The $C_1$ to $C_4$ alcohol is used in an amount from 10 to 40 wt %, preferably from 20 to 30 wt % and particularly from 25 to 30 wt %. Suitable alcohols are, for example, methanol, ethanol, isopropanol, n-propanol and butanol, of which ethanol and isopropanol are particularly preferred.

The water content is from 10 to 30 wt %, particularly from 15 to 25 wt % and particularly from 20 to 25 wt %.

Acetone, methyl acetate or a mixture thereof is used as cosolvent in an amount from 1 to 30 wt %, preferably from 5 to 15 wt .% and particularly from 5 to 10 wt %. Particularly preferred is acetone. The comparative experiments described hereinbelow show a number of positive effects achieved by use of acetone in aqueous-alcoholic aerosol hair sprays. It was surprising to find not only that the abovesaid negative properties of acetone are suppressed in the solvent/propellant system of the invention, but that additionally a number of improvements are attained, particularly in regard to drop formation, drop size, wetness, drying time and the feel of the polymer film.

Suitable propellants are primarily the usual, known aerosol propellants, for example the lower alkanes, for example n-butane, i-butane and propane, or their mixtures, and dimethyl ether or fluorocarbons, such as F 152a (1,1-difluoroethane) or F 134 (tetrafluoroethane) as well as propellants which at the pressures involved are in gaseous form, for example $N_2$, $N_2$ and $CO_2$, and mixtures of the aforesaid propellants.

The preferred propellant system, however, is a mixture of dimethyl ether and a fluorocarbon, the properties of which, particularly in terms of drop size and drying time, are further modified by the vapor pressures of the lower alcohols used as solvent and by the vapor pressure of the cosolvent, vapor pressures which at room temperature are not insignificant. Dimethyl ether is used in an amount from 15 to 45 wt %, preferably from 25 to 35 wt % and particularly from 30 to 35 wt %. The fluorocarbons are used in an amount from 5 to 30 wt %, preferably from 5 to 15 wt % and particularly from 5 to 10 wt %. Suitable fluorocarbons are 1,1-difluoroethane and 1,1,1,2-tetrafluoroethane, of which 1,1 -difluoroethane is preferred. The ratio of dimethyl ether to fluorocarbon ideally ranges from 1.5:1 to 9:1, preferably from 3:1 to 7:1 and particularly from 3:1 to 5:1, the total propellant content being from 20 to 75 wt %, preferably from 30 to 55 wt % and particularly from 35 to 45 wt%.

The hair spray composition according to the invention is introduced into a commercial pressure container made either of noncorroding material or a material which is internally coated to prevent corrosion or contains at least one corrosion inhibitor.

The hair spray according to the invention gives the best results when the spray system is so designed that the product discharge rate is from 3.5 g to 5.5 g, and preferably from 4 to 5 g, per 10 seconds of spraying time, and a valve with a side bore (vapor phase housing) and a spray head with a soft swirl nozzle are used.

The hair spray composition according to the invention can contain other additives commonly used in cosmetics, for example softeners such as glycerol, glycol or phthalate esters; odorants and perfumes, photostabilizers, UV screens, hair-care additives, combability improvers, humectants, dyes, corrosion inhibitors, antioxidants and preservatives, in an amount from 0.01 to 10% each and in a total amount from 0.01 to 20 wt %.

The hair spray according to the invention is characterized in that it makes possible the preparation of low-cost aerosol hair sprays containing a maximum of 55% VOCs while at the same time exhibiting good use properties. It contains a relatively low amount of the relatively expensive non-VOC fluoro-carbon propellants, while still exhibiting good use properties, particularly a degree of wetness that is not excessive, a reduced curl droop effect and acceptable drying rates.

The following examples provide a further illustration of the object of the invention.

EXAMPLES

All polymer quantities given in the following examples are based on the solids content.

Example 1

55% Voc Aerosol Hair Spray

| | |
|---|---|
| 6.0 g | of PVP/vinylcaprolactam/DMAPMA/acrylate copolymer (Aquaflex ® SF 40, by ISP) |
| 5.0 g | of acetone |
| 25.0 g | of ethanol |
| 24.0 g | of water |
| 30.0 g | of dimethyl ether |
| 10.0 g | of hydrofluorocarbon [HFC] 152a (1,1-difluoroethane) |
| 100.0 g | |

The composition was introduced into an aerosol can fitted with a valve with vapor phase housing (Precision, housing 0.050"×0.013") and a capillary dip tube (0.060"/0.133"). The tapered bore was 1×0.013". A spray head with a 0.016" soft swirl nozzle was used. The product discharge rate was 4.5 g for 10 s of spraying time.

Example 2

55% Voc Aerosol Hair Spray

| | |
|---|---|
| 6.0 g | of PVP/VA |
| 10.0 g | of acetone |
| 25.0 g | of ethanol |
| 14.0 g | of water |
| 30.0 g | of dimethyl ether |
| 15.0 g | of HFC 152a (1,1-difluoroethane) |
| 100.0 g | |

An aerosol can was filled as in Example 1.

Example 3

55% Voc Aerosol Hair Spray

| | |
|---|---|
| 5.0 g | of acrylates copolymer (Balance ® Extra, by National Starch) |
| 0.3 g | of aminomethylpropanol |
| 15.0 g | of acetone |
| 30.0 g | of ethanol |
| 19.7 g | of water |
| 25.0 g | of dimethyl ether |
| 5.0 g | of HFC 134a (tetrafluoroethane) |
| 100.0 g | |

An aerosol can was filled as in Example 1.

Example 4

5% Voc Aerosol Hair Spray

| | |
|---|---|
| 7.0 g | of acrylates/hydroxy ester acrylate copolymer (Acudyne ® 258, by Rohm & Haas) |
| 0.7 g | of aminomethylpropanol |
| 5.0 g | of methyl acetate |
| 20.0 g | of ethanol |
| 22.3 g | of water |
| 35.0 g | of dimethyl ether |
| 10.0 g | of HFC 152a (1,1-difluoroethane) |
| 100.0 g | |

An aerosol can was filled as in Example 1.

Example 7

Comparative Example

An acetone-containing aerosol hair spray according to the invention, 5A, was compared with an analogous hair spray 5B devoid of acetone, i.e., not according to the invention. The exact compositions are shown in Table 1. The aerosol cans were filled as in Example 1.

TABLE 1

| COMPOSITIONS TESTED | | |
|---|---|---|
| | 5A | 5B |
| PVP/vinylcaprolactam/CMAPMA/acrylate copolymer (Aquaflex ® SF 40, by ISP) | 5 g | 5 g |
| Ethanol | 25 g | 25 g |
| Water | 25 g | 30 g |
| Acetone | 5 g | — |
| Dimethyl ether | 30 g | 30 g |
| HFC 152a (1,1-difluoroethane) | 10 g | 10 g |

In one-side tests, one half of the hair of a test person was sprayed with hair spray 5A according to the invention and the other half with hair spray 5B, not according to the invention. The sprayed hair was evaluated by professional hair dressers. According to this evaluation, hair spray 5A according to the invention was rated superior in terms of all the following criteria:

| | |
|---|---|
| Drop formation | (positive, few drops are visible on the sprayed hair; negative: many drops are visible) |
| Drop size | (positive: small drops; negative: large drops) |
| Wetness | (positive: slight moistening of the hair; negative: marked moistening of the hair) |
| Drying time | (positive: short drying time; negative: long drying time) |
| Feel of resin film (hand) | (positive: pleasant, natural feel; negative: stiff or tacky, unnatural feel. |

We claim:

1. An aerosol hair spray product consisting of a pressurized container, an aerosol hair spray composition contained in the pressurized container and a spraying device for dispensing said composition from said pressurized container, said aerosol hair spray composition comprising
   at least one hair-setting polymer,
   from 10 to 40% by weight, based on a total amount of said composition, of at least one alcohol with from one to four carbon atoms,
   from 10 to 30% by weight, based on said total amount of said composition, water,
   from 1 to 30% by weight, based on said total amount of said composition, of at least one volatile cosolvent selected from the group consisting of acetone and methyl acetate,
   from 15 to 45% by weight, based on said total amount of said composition, of dimethyl ether, and
   from 5 to 30% by weight, based on said total amount of said composition, of at least one non-VOC propellant selected from the group consisting of fluorocarbons.

2. The aerosol hair spray product as defined in claim 1, wherein said composition contains from 20 to 30% by weight, based on said total amount of said composition, of said at least one alcohol, 15 to 25% by weight, based on said total amount of said composition, of said water 5 to 15% by weight, based on said total amount of said composition of said at least one volatile cosolvent, from 25 to 35% by weight based on said total amount of said composition, of said dimethyl ether and from 5 to 15% by weight, based on said total amount of said composition, of said at least one non-VOC propellant.

3. The aerosol hair spray product as defined in claim 1, wherein said spraying device has a valve with a side bore and said valve, said pressurized container and said composition are formed so as to provide a product discharge rate from 3.5 to 5.5 g per 10 sec of spraying time when said valve is opened to dispense said composition from the container.

4. The aerosol hair spray product as defined in claim 1, wherein said composition contains from 3 to 20% by weight, based on said total amount of said composition, of said at least one hair-setting polymer.

5. The aerosol hair spray product as defined in claim 1, wherein said at least one alcohol is selected from the group consisting of ethanol and isopropanol.

6. The aerosol hair spray product as defined in claim 1, wherein said at least one non-VOC propellant is selected from the group consisting of 1,1-difluoro-ethane and 1,1,1,2-tetrafluoroethane.

7. The aerosol hair spray product as defined in claim 1, wherein said at least one volatile cosolvent consists of acetone.

8. The aerosol hair spray product as defined in claim 1, wherein said hair spray composition contains no more than 55% by weight volatile organic compounds.

* * * * *